United States Patent [19]

Givens

[11] 4,388,266
[45] Jun. 14, 1983

[54] METHOD AND SYSTEM FOR MONITORING ORE GRADE OF AN URANIUM BEARING MIXTURE

[75] Inventor: Wyatt W. Givens, Dallas, Tex.

[73] Assignee: Mobil Oil Corporation, New York, N.Y.

[21] Appl. No.: 187,926

[22] Filed: Sep. 17, 1980

[51] Int. Cl.³ .......................................... G01N 23/12
[52] U.S. Cl. .................................................. 376/164
[58] Field of Search ........................ 376/159, 164, 257

[56] References Cited

U.S. PATENT DOCUMENTS

| | | | |
|---|---|---|---|
| 3,018,374 | 1/1962 | Britchett | 376/159 |
| 3,456,113 | 7/1969 | Keepin | 376/159 |
| 3,686,503 | 8/1972 | Givens et al. | 250/83.1 |
| 3,688,117 | 8/1972 | Givens | 376/164 |
| 3,823,316 | 7/1974 | Boswell | 376/159 |
| 3,828,189 | 8/1974 | Givens | 376/164 |

OTHER PUBLICATIONS

S 2857004, 8th Ann. Conf. & Ex. Appl. Marn. Tech. to Human Needs, Wash. D.C. (11–13 Sep. 1972), Noakes et al., pp. 8415–8428.
Radiochem. Radioanal. Lett., 6/6/381–388 (1971), Hayward et al.

*Primary Examiner*—Sal Cangialosi
*Attorney, Agent, or Firm*—Charles A. Huggett; Michael G. Gilman; G. W. Hager

[57] ABSTRACT

A method and system for monitoring the ore grade of an uranium bearing fluid mixture. A sample of the fluid mixture is irradiated with neutrons. Delayed fission neutrons resulting from the fission of uranium present in the sample are counted as an indication of uranium ore grade.

2 Claims, 3 Drawing Figures

METHOD AND SYSTEM FOR MONITORING ORE GRADE OF AN URANIUM BEARING MIXTURE

BACKGROUND OF THE INVENTION

One technique for the mining of uranium is with a borehole slurry mining tool. In such a mining operation, water provides the cutting jet and also powers a pump in the mining tool for bringing the slurry to the surface. After being brought to the surface, the slurry is stored in a slurry pond. The solids settle to the bottom of the slurry pond and water is pumped from the pond and recycled through the mining tool.

SUMMARY OF THE INVENTION

In accordance with the present invention, there is provided a method and system for monitoring the ore grade of an uranium bearing, fluid mixture. A sample of the uranium bearing mixture is selected and irradiated with neutrons. Delayed fission neutrons resulting from the fission of uranium present in the selected sample are counted.

In a more specific aspect, the ore grade of an uranium bearing slurry produced in the mining of a subsurface uranium bearing formation is monitored. The slurry is transported from the subsurface formation to a slurry pit on the earth's surface for storage. A portion of the slurry is sampled as it is transported from the subsurface formation to the slurry pit. The sample slurry is irradiated with neutrons to induce fission of the uranium present in the sampled slurry. Delayed fission neutrons resulting from the fission of uranium present in the sampled slurry are counted. The length of the transporting means and the flow rate of the slurry between the irradiation and counting locations may be selected to accentuate the counting of delayed neutrons at a time after irradiation equal to about the half life of a selected one of the predominate delayed fission neutron groups of the uranium. The sampled slurry is then discharged into the slurry pit.

The mined slurry may be periodically sampled at selective time intervals during the mining operation. Each selected sample is irradiated with neutrons, the resulting delayed fission neutrons are counted, and the sample is then discharged into the slurry pit. This monitoring of the slurry mining operation provides a means for identifying the quantity of uranium mined and for indicating when the ore grade of the uranium has become too low to economically justify further mining operations.

DESCRIPTION OF THE PREFERRED EMBODIMENT

The present invention is directed toward a method and system for monitoring the uranium content of a fluid mixture, and more particularly of the slurry obtained in a slurry mining operation so that mining can be terminated when the uranium concentration becomes too low to justify further mining.

Figure 1:
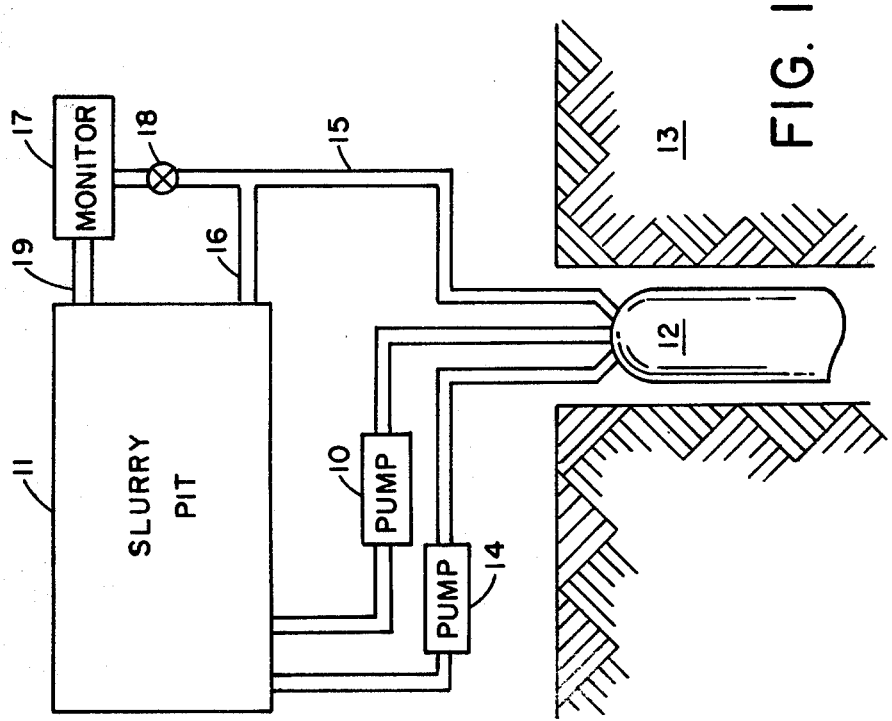
FIG. 1 illustrates the uranium slurry mining operation of the present invention.

Referring to FIG. 1 there is illustrated a slurry mining operation employing the uranium contents monitoring procedure of the present invention. The pump 10 extracts water from the slurry pit 11 for use as a cutting jet of the mining tool 12 located within the formation 13 being mined for uranium. The pump 14 extracts water from the slurry pit and supplies it to the mining tool 12 for use in bringing the slurry to the surface of the earth. This slurry then passes through the channels 15 and 16 for discharge to the slurry pit 11. The solids settle in the bottom of the slurry pit and the water is then recirculated through the mining operation by means of the pumps 10 and 14. The settled slurry, with its increased percentage of solids, is removed from the settling pond and uranium is extracted by conventional means. It is a specific feature of the present invention to monitor the discharged slurry for uranium content so that the cumulative amount of mined uranium is identified and the mining operation can be terminated when the ore grade becomes too low to economically justify further mining. The solids content of the slurry being discharged into the slurry pit will be in the order of 20%. The mining operation becomes uneconomical when the uranium ore content is about 0.05% of the solids content. Consequently, the monitoring procedure for the uranium content needs to have a sensitivity of about 0.01%. To carry out this monitoring procedure there is provided the monitor 17 into which a portion of the mined slurry passes by way of valve 18. After being monitored for uranium ore content, the slurry is discharged into the slurry pit by way of channel 19.

Figure 2:
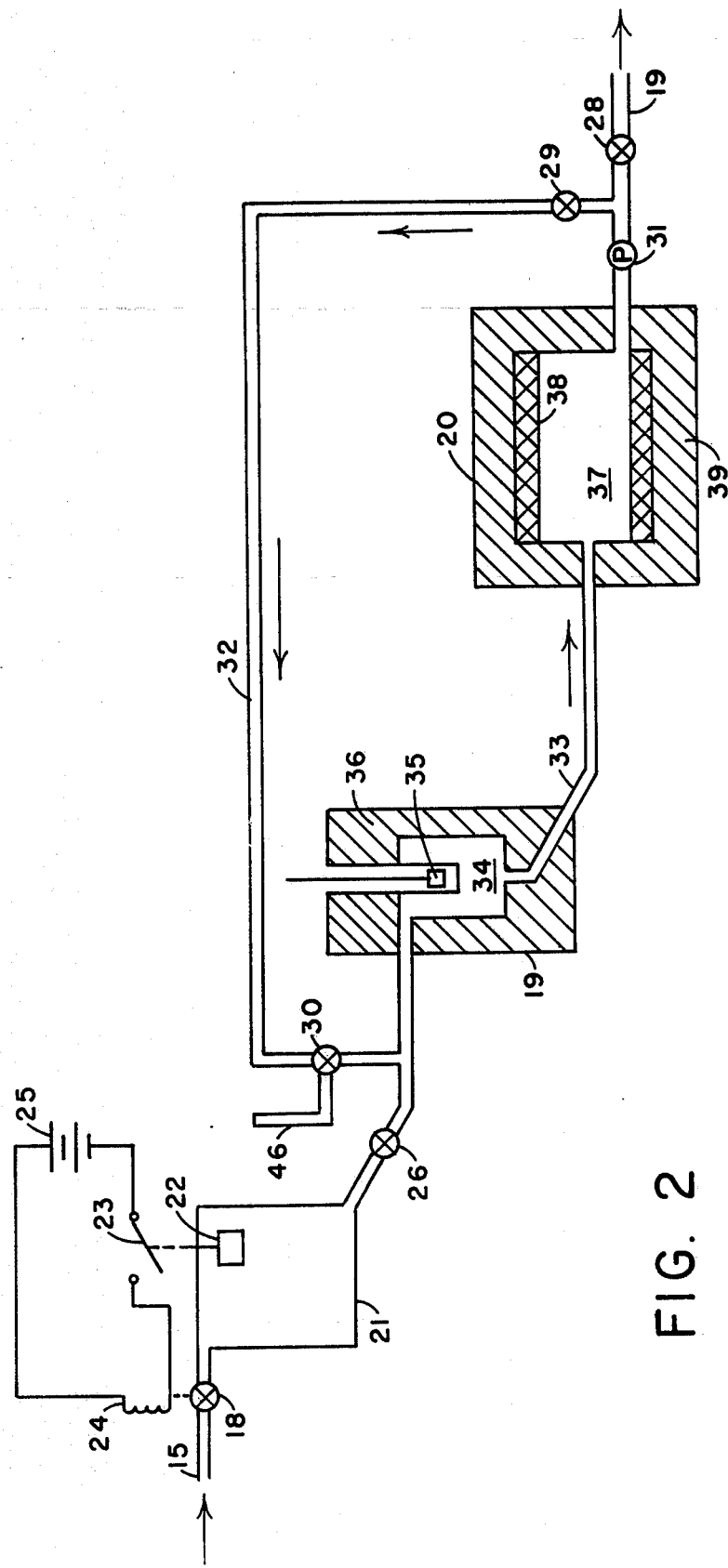
FIG. 2 illustrates a slurry contents monitor for use in conjunction with the uranium slurry mining operation of FIG. 1.

Referring now to FIG. 2 there is illustrated in detail the monitor 17 of the present invention. After a certain quantity of slurry passes into the monitor 17, the valve 18 is closed and the slurry is recycled in a closed loop through an activation cell 19 and a counting cell 20. The recycling is continued to provide a statistically good response at the lowest cut-off concentration required for the uranium content in the slurry. The desired cutoff ore grade determines the number of activation and count cycles n. Accordingly, each slurry sample, regardless of ore grade, will be subjected to n activation and count cycles.

Upon passing through the valve 18 the slurry enters the holding tank 21 and, with valve 26 closed, fills to a designated level as determined by float 22. When the designated fluid level is reached, float 22 closes the switch 23 thereby energizing solenoid 24 from the battery power supply 25. Upon such energization valve 18 is closed. Valves 26, 29 and 30 are opened and valve 28 closed to allow slurry to flow into the activation cell 19 and the counting cell 20. Pump 31 is activated to continuously recycle the slurry through the activation and counting cells during the monitoring operation. At this time the monitoring operation can begin.

Upon completion of the monitoring operation valves 29 and 30 are closed and valves 26 and 28 opened to allow pumping of the slurry through the discharge channel 19 into the slurry pit. The volume of the holding tank is preferably 2 to 3 times that of the combined volumes of the activation cell 19, counting cell 20, and the circulation channels 32 and 33. In one embodiment the holding tank volume is about 14 gallons and the volume of the activation cell, counting cell, and circulation channels about 6 gallons. Channel 32 is elevated so that the system is cleaned through gravity feed. Vent 46 purges the circulation loop of air.

Inserted into the slurry containing chamber 34 of the activation cell 19 is the continuous neutron source 35 such as a Californium-252, Americum-Beryllium, or other similar source. Surrounding this chamber is a moderator and shielding material 36 (such as polyethylene or other hydrogenous material). Surrounding the slurry containing chamber 37 of the counting cell 20 is the circular array of neutron counters 38 operated in parallel, helium-3 counters being particularly sensitive to thermal neutrons. Also surrounding this chamber 37 is a moderator and shielding material 39.

In practice, the neutron source 35 irradiates the slurry within the activation cell 19. Such slurry is then transported to the counting cell 20 where the neutron counters 38 measure the delayed fission neutrons of the uranium content within the slurry. Such delayed neutrons are produced in the fission process within a few milliseconds after irradiation of the slurry by the neutron source 35. In the preferred embodiment, a Californium-252 source is employed having an average energy of about 2.3 Mev. Neutrons greater than about 2.0 Mev induce fission in uranium-238 and thermal neutrons induce fission in uranium-235. In this embodiment, therefore, most of the fission will be from the uranium-235 content of the slurry. The major delayed fission neutron groups that result from uranium-235 fission and their relative contributions are shown in the following table:

| Group | Half-life (sec.) | Relative Abundance |
|---|---|---|
| 1 | 55.72 | 0.033 |
| 2 | 22.72 | 0.219 |
| 3 | 6.22 | 0.196 |
| 4 | 2.30 | 0.395 |
| 5 | 0.61 | 0.115 |
| 6 | 0.23 | 0.042 |

With no recycling of the slurry through the activation cell 19 and counting cell 20, the distance rate of the fluid through the line and the flow between the activation cell 19 and the counting cell 20 may be adjusted to accentuate these six predominate delayed fission neutrons. For example, the two predominate groups occur at half lives at about 2.3 and 6.2 seconds. Accordingly, the counting cell 20 may be spaced from the activation cell 19 such that the fluid mixture arrives at the neutron counters 38 within the counting cell 20 at 2.3 or 6.2 seconds after being irradiated by the neutron source 35 within the activation cell 19.

In the event there is recycling of the slurry through the activation cell 19 and the counting cell 20, the six neutron group half-lives and their relative contributions of delayed fission neutrons build up under prolonged bombardment due to recycling of the slurry through the activation and counting cells until they all appear as a single neutron group with an effective half-life of about 13.9 seconds.

After repeated bombardments of the slurry by means of the neutron source 35, the accumulated count of the counter 38 can be represented as follows:

$$\text{Count} = \frac{NfGE}{\lambda} (1 - e^{-\lambda t_b})(e^{-\lambda t_w})(1 - e^{-\lambda t_c}) \times$$

-continued $$\left[ \frac{n}{(1 - e^{-\lambda T})} - \frac{e^{-\lambda T}(1 - e^{-n\lambda T})}{(1 - e^{-\lambda T})^2} \right]$$

where N = number of uranium atoms per cc.
 fGE/λ = a constant,
 $(1 - e^{-\lambda t_b})$ = the activity build up during the time $t_b$, the slurry residence time in the activation cell,
 $e^{-\lambda t_w}$ = the activity decay during transport of the slurry from the activation cell to the counting cell,
 $(1 - e^{-\lambda t_c})$ = cummulative activity counted during the time $t_c$, the slurry residence time in the counting cell.
 T = the cycle period, and
 n = the number of cycles.

The term:

$$\frac{n}{(1 - e^{-\lambda T})} - \frac{e^{-\lambda T}(1 - e^{-n\lambda T})}{(1 - e^{-\lambda T})^2}$$

is a gain factor that is characteristic of cyclic activation on the counting accumulation, and can be represented by the term:

$$n(n+1)/2$$

when the cycle period T is short compared to the average activity half life.

Figure 3:
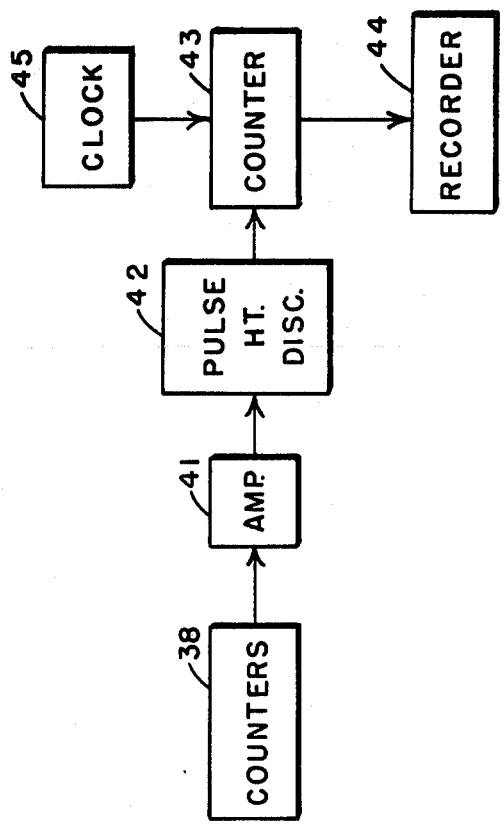
FIG. 3 is a schematic diagram of circuitry utilized in the control of the monitor of FIG. 2.

Referring now to FIG. 3, there is illustrated the circuitry for operating in conjunction with neutron source 35 and neutron counter 38 to carry out the accumulated count set forth in expression (1) above. The counters 38 are connected in parallel through the amplifier 41 and the pulse height discriminator 42 to the counter 43. Pulse height discriminator 42 is adjusted to pass to the counter 43 those pulses produced by the counters 38. The accumulated count is proportional to the uranium concentration in the slurry. Through standard calibration procedures the accumulated count can be converted to an absolute uranium concentration. Counter 43 is turned on at the time pump 31 is turned on and operates for a predetermined total time nT. After monitoring is complete, valves 29 and 30 are closed and valves 26 and 28 opened to discharge the slurry into the slurry pit.

The number of activation-count cycles n, with a cycle time T, is determined by the lowest concentration of uranium of interest. Both monitoring and calibration assays are run for the same time period nT. One concentration is recorded in conjunction with a flow meter in the slurry and the accumulated ore mined is determined. Should the ore grade or concentration fall to some minimum value, slurry mining is terminated either in the direction of the mining tool or in the particular borehole. After n activation count cycles, the monitored slurry is discharged through the valve 28 and channel 19 into the slurry pit. Upon completion of such discharge, the monitoring system is again filled with slurry from the channel 15 and another activation and counting operation initiated. Such monitoring operations may be repeated until the delayed fission neutron count indicates that the uranium ore grade has become too low to economically justify further uranium slurry mining operations.

The foregoing has described an uranium monitoring operation employing the method and system of the invention. It is to be understood that various modifications to the disclosed embodiment, as well as the monitoring of uranium bearing mixtures other than in an uranium slurry mining operation, may become apparent to one skilled in the art without departing from the scope and spirit of the invention as hereinafter defined by the appended claims.

I claim:

1. A method of monitoring the ore grade of an uranium bearing fluid mixture comprising the steps of:
    (a) transporting an uranium bearing fluid mixture past a source of neutrons so as to permit continuous irradiation of said fluid mixture with fast neutrons,
    (b) transporting said irradiated fluid mixture past a single neutron counter, and
    (c) recycling said uranium bearing fluid mixture past said neutron source and said single neutron counter to affect a build-up of delayed fission neutrons such that the predominate delayed fission neutron groups of uranium-235 appear as a single neutron group to said single neutron counter with an effective half-life at about 13.9 seconds.

2. A system for monitoring the ore grade of an uranium bearing fluid mixture, comprising:
    (a) a neutron source for continuously irradiating an uranium bearing fluid mixture with neutrons,
    (b) a single counter for counting fission neutrons resulting from the fission of uranium present in said fluid mixture,
    (c) means for recycling said fluid mixture past said neutron source and said single neutron counter such that the continued irradiation from recycling of the fluid mixture past the neutron source causes build up of delayed fission neutrons from uranium-235 to the extent that the predominate neutron half-life groups appear as a single neutron group with an effective half-life at about 13.9 seconds and,
    (d) means for controlling the travel time of the fluid mixture between the neutron source and the single neutron counter during recycling to about 13.9 seconds.

* * * * *